US006475749B1

(12) United States Patent
Morrison et al.

(10) Patent No.: US 6,475,749 B1
(45) Date of Patent: Nov. 5, 2002

(54) RH HYBRID ANTIBODY

(75) Inventors: Sherie L. Morrison, Los Angeles, CA (US); Ramon Montaño, Miranda (VE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/372,425

(22) Filed: Aug. 11, 1999

(51) Int. Cl.$^7$ .................. C12P 21/08; G01N 33/555
(52) U.S. Cl. ............... 435/7.25; 435/7.2; 530/387.3; 530/388.7
(58) Field of Search ............ 530/387.3, 388.7; 435/7.2, 7.25

(56) References Cited

U.S. PATENT DOCUMENTS

| | | |
|---|---|---|
| 4,296,090 A | 10/1981 | Graham, Jr. et al. |
| 4,319,882 A | 3/1982 | Sharma |
| 4,358,436 A | 11/1982 | Graham, Jr. et al. |
| 4,403,042 A | 9/1983 | Henry et al. |
| 4,851,210 A | 7/1989 | Hewett |
| 5,593,675 A | 1/1997 | Hodler et al. |
| 5,653,978 A | 8/1997 | De Burgh Bradley et al. |
| 5,723,293 A | 3/1998 | Huang |
| 5,840,585 A | 11/1998 | Rodkey et al. |

FOREIGN PATENT DOCUMENTS

WO    WO 97/47732    * 12/1997

OTHER PUBLICATIONS

McCann et al. J. Immunol. Methods 115:3–15, Nov. 1988.*
Smith, R.I.F. et al., "Recombinant Polymeric IgG: An Approach to Engineering More Potent Antibodies," *Biotechnology*, vol. 1, pp. 683–688 (1994).
Smith, R.I.F. et al., Addition of a µ–Tailpiece to IgG Results in Polymeric Antibodies with Enhanced Effector Functions Including Complement–Mediated Cytolysis by IgG4, *The Journal of Immunology*, pp. 2226–2236 (1994).

* cited by examiner

*Primary Examiner*—Christina Chan
*Assistant Examiner*—Amy DeCloux
(74) *Attorney, Agent, or Firm*—Shapiro & Dupont LLP (57) ABSTRACT

Rh antibody hybrids for use in testing red blood cells for the presence of one or more Rh factors. The Rh hybrid antibody may also be used in therapeutic procedures which require the use of Rh antisera. The hybrid antibody includes an IgG anti-Rh antibody which has a polymeric tailpiece attached to the carboxy terminal end of each of the IgG antibody heavy chains. A hemagglutinin method is provided for Rh phenotyping in which agglutination of Rh-positive red blood cells is achieved in a one-step process involving addition of the hybrid Rh antisera to the red blood cells being tested.

2 Claims, 2 Drawing Sheets

FIG. 1

7629pAN-CMV/huG3utp/VantiD/tara
(11415 bp)

```
                          SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 2674 nucleotides
        (B) TYPE: nucleotide
        (C) STRANDEDNESS: single
        (D) TOPOLOGY: linear (ii) MOLECULE TYPE: Heavy chain with Tailpiece - DNA
            (with introns)

(ix) SEQUENCE DESCRIPTION: SEQ ID NO: 1:

ATGAAACACC TGTGGTTCTT CCTCCTCCTG GTGGCAGCTC CCAGATGGGT CCTGTCCCAG      60

GTGCAGCTAC AGCAGTGGGG CGCAGGACTG TTGAAGCCTT CGGAGACCCT GTCCCTCACC     120

TGCGCTGTCT ATGGTGGGTC CTTCAGTGGT CACCACTGGA GTTGGATCCG CCAGCCCCCA     180

GGGAAGGGGC TGGAGTGGAT TGGAGAAATC GATCATAGTG AAGCACCAA  TTACAACCCG     240

TCCCTCAAGA GTCGAGTCAC CATATCAGTA GACACGTCCA AGAACCAGTT CTCCGTGAAG     300

CTGACCTCTG TGACCGCCGC GGACACGGCT GTGTATTACT GTGCGAGAAG CCGGCATTGT     360

ACAAGTATCA GCTGTTTTCA GTATTATTTA GGATACTACT ACTACTACAT GGACGTCTGG     420
```

-continued

```
GGCAAAGGGA CCACGGTCAC CGTCTCCTCA GCTAGCACCA AGGGCCCATC GGTCTTCCCC    480

CTGGCGCCCT GCTCCAGGAG CACCTCTGGG GGCACAGCGG CCCTGGGCTG CCTGGTCAAG    540

GACTACTTCC CCGAACCGGT GACGGTGTCG TGGAACTCAG GCGCCCTGAC CAGCGGCGTG    600

CACACCTTCC CGGCTGTCCT ACAGTCCTCA GGACTCTACT CCCTCAGCAG CGTGGTGACC    660

GTGCCCTCCA GCAGCTTGGG CACCCAGACC TACACCTGCA ACGTGAATCA CAAGCCCAGC    720

AACACCAAGG TGGACAAGAG AGTTGGTGAG AGGCCAGCGC AGGGAGGGAG GGTGTCTGCT    780

GGAAGCCAGG CTCAGCCCTC CTGCCTGGAC GCATCCCGGC TGTGCAGTCC CAGCCCAGGG    840

CACCAAGGCA GGCCCCGTCT GACTCCTCAC CCGGAGGCCT CTGCCCGCCC CACTCATGCT    900

CAGGGAGAGG GTCTTCTGGC TTTTTCCACC AGGCTCCGGG CAGGCACAGG CTGGATGCCC    960

CTACCCCAGG CCCTTCACAC ACAGGGGCAG GTGCTGCGCT CAGAGCTGCC AAGAGCCATA   1020

TCCAGGAGGA CCCTGCCCCT GACCTAAGCC CACCCCAAAG GCCAAACTCT CTACTCACTC   1080

AGCTCAGACA CCTTCTCTCT TCCCAGATCT GAGTAACTCC CAATCTTCTC TCTGCAGAGC   1140

TCAAAACCCC ACTTGGTGAC ACAACTCACA CATGCCCACG GTGCCCAGGT AAGCCAGCCC   1200

AGGCCTCGCC CTCCAGCTCA AGGCGGGACA AGAGCCCTAG AGTGGCCTGA GTCCAGGGAC   1260

AGGCCCCAGC AGGGTGCTGA CGCATCCACC TCCATCCCAG ATCCCCGTAA CTCCCAATCT   1320

TCTCTCTGCA GAGCCCAAAT CTTGTGACAC ACCTCCCCCG TGCCCAAGGT GCCCAGGTAA   1380

GCCAGCCCAG GCCTCGCCCT CCAGCTCAAG GCAGGACAGG TGCCCTAGAG TGGCCTGAGT   1440

CCAGGGACAG GCCCCAGCAG GGTGCTGACG CATCCACCTC CATCCCAGAT CCCCGTAACT   1500

CCCAATCTTC TCTCTGCAGA GCCCAAATCT TGTGACACAC CTCCCCCGTG CCCAAGGTGC   1560

CCAGGTAAGC CAGCCCAGGC CTCGCCCTCC AGCTCAAGGC AGGACAGGTG CCCTAGAGTG   1620

GCCTGAGTCC AGGGACAGGC CCCAGCAGGG TGCTGACGCA TCCACCTCCA TCCCAGATCC   1680

CCGTAACTCC CAATCTTCTC TCTGCAGAGC CCAAATCTTG TGACACACCT CCCCGTGCC   1740

CAAGGTGCCC AGGTAAGCCA GCCCAGGCCT CGCCCTCCAG CTCAAGGCAG GACAGGTGCC   1800

CTAGAGTGGC CTGCATCCAG GGACAGGTCC CAGTCGGGTG CTGACACATC TGCCTCCATC   1860

TCTTCCTCAG CACCTGAACT CCTGGGAGGA CCGTCAGTCT TCCTCTTCCC CCCAAAACCC   1920

AAGGATACCC TTATGATTTC CCGGACCCCT GAGGTCACGT GCGTGGTGGT GGACGTGAGC   1980

CACGAAGACC CCGAGGTCCA GTTCAAGTGG TACGTGGACG GCGTGGAGGT GCATAATGCC   2040

AAGACAAAGC TGCGGGAGGA GCAGTACAAC AGCACGTTCC GTGTGGTCAG CGTCCTCACC   2100

GTCCTGCACC AGGACTGGCT GAACGGCAAG GAGTACAAGT GCAAGGTCTC CAACAAAGCC   2160

CTCCCAGCCC CCATCGAGAA AACCATCTCC AAAGCCAAAG GTGGGACCCG CGGGGTATGA   2220

GGGCCACGTG GACAGAGGCC AGCTTGACCC ACCCTCTGCC CTGGGAGTGA CCGCTGTGCC   2280

AACCTCTGTC CCTACAGGAC AGCCCCGAGA ACCACAGGTG TACACCCTGC CCCCATCCCG   2340

GGAGGAGATG ACCAAGAACC AGGTCAGCCT GACCTGCCTG GTCAAAGGCT TCTACCCCAG   2400

CGACATCGCC GTGGAGTGGG AGAGCAATGG GCAGCCGGAG AACAACTACA ACACCACGCC   2460

TCCCATGCTG GACTCCGACG GCTCCTTCTT CCTCTACAGC AAGCTCACCG TGGACAAGAG   2520

CAGGTGGCAG CAGGGGAACA TCTTCTCATG CTCCGTGATG CATGAGGCTC TGCACAACCG   2580

CTACACCCAG AAGAGCCTCT CCCTGAGTAC TGGTAAACCC ACCCTGTACA ACGTGTCCCT   2640

GGTCATGTCC GACACAGCTG GCACCTGCTA CTGA                               2674
```

(2) INFORMATION FOR SEQ ID NO: 2:

(i) SEQUENCE CHARACTERISTICS:
        (A) LENGTH: 447 amino acids
        (B) TYPE: amino acid
        (C) STRANDEDNESS: single
        (D) TOPOLOGY: linear     (ii) MOLECULE TYPE: Heavy chain with Tailpiece - AA     (ix) SEQUENCE DESCRIPTION: SEQ ID NO: 2:

```
Met Lys His Leu Trp Phe Phe Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly His His Trp Ser Trp Ile Arg Gln Pro Pro Gly Lys Gly Leu
        50                  55                  60

Glu Trp Ile Gly Glu Ile Asp His Ser Glu Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Val Lys Leu Thr Ser Val Thr Ala Ala Asp Thr Ala Val Tyr
                100                 105                 110

Tyr Cys Ala Arg Ser Arg His Cys Thr Ser Ile Ser Cys Phe Gln Tyr
            115                 120                 125

Tyr Leu Gly Tyr Tyr Tyr Tyr Met Asp Val Trp Gly Lys Gly Thr
130                 135                 140

Thr Val Thr Val Ser Ser Glu Leu Lys Thr Pro Leu Gly Asp Thr Thr
145                 150                 155                 160

His Thr Cys Pro Arg Cys Pro Glu Pro Lys Ser Cys Asp Thr Pro Pro
                165                 170                 175

Pro Cys Pro Arg Cys Pro Glu Pro Lys Ser Cys Asp Thr Pro Pro
            180                 185                 190

Cys Pro Arg Cys Pro Glu Pro Lys Ser Cys Asp Thr Pro Pro Pro Cys
            195                 200                 205

Pro Arg Cys Pro Ala Pro Glu Leu Leu Gly Gly Pro Ser Val Phe Leu
    210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Gln
                245                 250                 255

Phe Lys Trp Tyr Val Asp Gly Val Glu Val His Asn Ala Lys Thr Lys
                260                 265                 270

Leu Arg Glu Glu Gln Tyr Asn Ser Thr Phe Arg Val Val Ser Val Leu
            275                 280                 285

Thr Val Leu His Gln Asp Trp Leu Asn Gly Lys Glu Tyr Lys Cys Lys
        290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
                325                 330                 335

Arg Glu Glu Met Thr Lys Asn Gln Val Ser Leu Thr Cys Leu Val Lys
                340                 345                 350
```

```
Gly Phe Tyr Pro Ser Asp Ile Ala Val Glu Trp Glu Ser Asn Gly Gln
        355                 360                 365
Pro Glu Asn Asn Tyr Asn Thr Thr Pro Pro Met Leu Asp Ser Asp Gly
        370                 375                 380
Ser Phe Phe Leu Tyr Ser Lys Leu Thr Val Asp Lys Ser Arg Trp Gln
385                 390                 395                 400
Gln Gly Asn Ile Phe Ser Cys Ser Val Met His Glu Ala Leu His Asn
                405                 410                 415
Arg Tyr Thr Gln Lys Ser Leu Ser Leu Ser Thr Gly Lys Pro Thr Leu
            420                 425                 430
Tyr Asn Val Ser Leu Val Met Ser Asp Thr Ala Gly Thr Cys Tyr
        435                 440                 445
```

(2) INFORMATION FOR SEQ ID NO: 3:

(i) SEQUENCE CHARACTERISTICS:
        (A) LENGTH: 705 nucleotides
        (B) TYPE: nucleotide
        (C) STRANDEDNESS: single
        (D) TOPOLOGY: linear     (ii) MOLECULE TYPE: Light chain - DNA     (ix) SEQUENCE DESCRIPTION: SEQ ID NO: 3:

```
ATGGCCTGGT CCCTACTGCT CACCCTTCTC ATTCACTGCA CAGGGTCCTG GGCCCAGTCT      60
GTGTTGACGC AGCCGCCCTC AGTGTCTGCG GCCCCAGGAC AGAAGGTCAC CATCTCCTGC     120
TCTGGAAGCA GCTCCAACAT TGGGAATAAT TATGTATCCT GGTACCAGCA TTTCCCAGGA     180
ACAGCCCCCA AACTTCTCAT TTATGACAAT AATCAGCGAC CCTCAGGGAT TCCTGACCGA     240
TTCTCTGGCT CCAAGTCTGG CACGTCAGCC ACCCTGGGCA TCACCGGACT CCAGACTGGG     300
GACGAAGCCG ATTATTACTG CGGAACATGG GATAGCAGCC TGAGTGCTGT GCTTTTCGGC     360
GGAGGGACCG AAGTGACCGT CCTAGGTCAG CCCAAGGCTG CCCCCTCGGT CACTCTGTTC     420
CCGCCGCCCT CCTCTGAGGA GCTTCAAGCC AACAAGGCCA CACTGGTGTG TCTCATAAGT     480
GACTTCTACC CGGGAGCCGT GACAGTGGCC TGGAAGGCAG ATAGCAGCCC CGTCAAGGCG     540
GGAGTGGAGA CCACCACACC CTCCAAACAA AGCAACAAGT ACGCGGCCAG CAGCTATCTG     600
AGCCTGACGC CTGAGCAGTG GAAGTCCCAC AGAAGCTACA GCTGCCAGGT CACGCATGAA     660
GGGAGCACCG TGGAGAAGAC AGTGGCCCCT ACAGAATGTT CATAG                    705
```

(2) INFORMATION FOR SEQ ID NO: 4:

(i) SEQUENCE CHARACTERISTICS:
        (A) LENGTH: 234 amino acids
        (B) TYPE: amino acid
        (C) STRANDEDNESS: single
        (D) TOPOLOGY: linear     (ii) MOLECULE TYPE: Light chain - AA     (ix) SEQUENCE DESCRIPTION: SEQ ID NO: 4:

```
Met Ala Trp Ser Leu Leu Leu Thr Leu Leu Ile His Cys Thr Gly Ser
                5                   10                  15
Trp Ala Gln Ser Val Leu Thr Gln Pro Pro Ser Val Ser Ala Ala Pro
            20                  25                  30
Gly Gln Lys Val Thr Ile Ser Cys Ser Gly Ser Ser Ser Asn Ile Gly
        35                  40                  45
Asn Asn Tyr Val Ser Trp Tyr Gln His Phe Pro Gly Thr Ala Pro Lys
```

-continued

```
              50                  55                  60
Leu Leu Ile Tyr Asp Asn Asn Gln Arg Pro Ser Gly Ile Pro Asp Arg
 65                  70                  75                  80

Phe Ser Gly Ser Lys Ser Gly Thr Ser Ala Thr Leu Gly Ile Thr Gly
                 85                  90                  95

Leu Gln Thr Gly Asp Glu Ala Asp Tyr Tyr Cys Gly Thr Trp Asp Ser
                100                 105                 110

Ser Leu Ser Ala Val Leu Phe Gly Gly Thr Glu Val Thr Val Leu
                115                 120                 125

Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Lys tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230                 234

(2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: IgM Tailpiece - AA (ix) SEQUENCE DESCRIPTION: SEQ ID NO: 5:

Pro Thr Leu Tyr Asn Val Ser Leu Val Met Ser Asp Thr Ala Gly Thr
                 5                  10                  15

Cys Tyr
 18

(2) INFORMATION FOR SEQ ID NO: 6:

(i) SEQUENCE CHARACTERISTICS:
        (A) LENGTH: 429 amino acids
        (B) TYPE: amino acid
        (C) STRANDEDNESS: single
        (D) TOPOLOGY: linear (ii) MOLECULE TYPE: Heavy chain without Tailpiece - AA (ix) SEQUENCE DESCRIPTION: SEQ ID NO: 6:

Met Lys His Leu Trp Phe Phe Leu Leu Leu Val Ala Ala Pro Arg Trp
                 5                  10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
                35                  40                  45

Ser Gly His His Trp Ser Trp Ile Arg Gln Pro Pro Gly Lys Gly Leu
    50                  55                  60
```

-continued

```
Glu Trp Ile Gly Glu Ile Asp His Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Val Lys Leu Thr Ser Val Thr Ala Ala Asp Thr Ala Val Tyr
            100                 105                 110

Tyr Cys Ala Arg Ser Arg His Cys Thr Ser Ile Ser Cys Phe Gln Tyr
        115                 120                 125

Tyr Leu Gly Tyr Tyr Tyr Tyr Met Asp Val Trp Gly Lys Gly Thr
    130                 135                 140

Thr Val Thr Val Ser Ser Glu Leu Lys Thr Pro Leu Gly Asp Thr Thr
145                 150                 155                 160

His Thr Cys Pro Arg Cys Pro Glu Pro Lys Ser Cys Asp Thr Pro Pro
                165                 170                 175

Pro Cys Pro Arg Cys Pro Glu Pro Lys Ser Cys Asp Thr Pro Pro Pro
            180                 185                 190

Cys Pro Arg Cys Pro Glu Pro Lys Ser Cys Asp Thr Pro Pro Pro Cys
        195                 200                 205

Pro Arg Cys Pro Ala Pro Glu Leu Leu Gly Gly Pro Ser Val Phe Leu
    210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Gln
                245                 250                 255

Phe Lys Trp Tyr Val Asp Gly Val Glu Val His Asn Ala Lys Thr Lys
            260                 265                 270

Leu Arg Glu Glu Gln Tyr Asn Ser Thr Phe Arg Val Val Ser Val Leu
        275                 280                 285

Thr Val Leu His Gln Asp Trp Leu Asn Gly Lys Glu Tyr Lys Cys Lys
    290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
                325                 330                 335

Arg Glu Glu Met Thr Lys Asn Gln Val Ser Leu Thr Cys Leu Val Lys
            340                 345                 350

Gly Phe Tyr Pro Ser Asp Ile Ala Val Glu Trp Glu Ser Asn Gly Gln
        355                 360                 365

Pro Glu Asn Asn Tyr Asn Thr Thr Pro Pro Met Leu Asp Ser Asp Gly
    370                 375                 380

Ser Phe Phe Leu Tyr Ser Lys Leu Thr Val Asp Lys Ser Arg Trp Gln
385                 390                 395                 400

Gln Gly Asn Ile Phe Ser Cys Ser Val Met His Glu Ala Leu His Asn
                405                 410                 415

Arg Tyr Thr Gln Lys Ser Leu Ser Leu Ser Thr Gly Lys
            420                 425             429
```

(2) INFORMATION FOR SEQ ID NO: 7:

(i) SEQUENCE CHARACTERISTICS:
        (A) LENGTH: 1341 nucleotides
        (B) TYPE: nucleotide
        (C) STRANDEDNESS: single
        (D) TOPOLOGY: linear (ii) MOLECULE TYPE: Heavy chains with tailpiece - DNA
        (without introns)

(ix) SEQUENCE DESCRIPTION: SEQ ID NO: 7:

| | | | | | |
|---|---|---|---|---|---|
| ATGAAACACC | TGTGGTTCTT | CCTCCTCCTG | GTGGCAGCTC | CCAGATGGGT | CCTGTCCCAG | 60 |
| GTGCAGCTAC | AGCAGTGGGG | CGCAGGACTG | TTGAAGCCTT | CGGAGACCCT | GTCCCTCACC | 120 |
| TGCGCTGTCT | ATGGTGGGTC | CTTCAGTGGT | CACCACTGGA | GTTGGATCCG | CCAGCCCCCA | 180 |
| GGGAAGGGGC | TGGAGTGGAT | TGGAGAAATC | GATCATAGTG | AAGCACCAA | TTACAACCCG | 240 |
| TCCCTCAAGA | GTCGAGTCAC | CATATCAGTA | GACACGTCCA | AGAACCAGTT | CTCCGTGAAG | 300 |
| CTGACCTCTG | TGACCGCCGC | GGACACGGCT | GTGTATTACT | GTGCGAGAAG | CCGGCATTGT | 360 |
| ACAAGTATCA | GCTGTTTTCA | GTATTATTTA | GGATACTACT | ACTACTACAT | GGACGTCTGG | 420 |
| GGCAAAGGGA | CCACGGTCAC | CGTCTCCTCA | GAGCTCAAAA | CCCCACTTGG | TGACACAACT | 480 |
| CACACATGCC | CACGGTGCCC | AGAGCCCAAA | TCTTGTGACA | CACCTCCCCC | GTGCCCAAGG | 540 |
| TGCCCAGAGC | CCAAATCTTG | TGACACACCT | CCCCCGTGCC | CAAGGTGCCC | AGAGCCCAAA | 600 |
| TCTTGTGACA | CACCTCCCCC | GTGCCCAAGG | TGCCCAGCAC | CTGAACTCCT | GGGAGGACCG | 660 |
| TCAGTCTTCC | TCTTCCCCCC | AAAACCCAAG | GATACCCTTA | TGATTTCCCG | GACCCCTGAG | 720 |
| GTCACGTGCG | TGGTGGTGGA | CGTGAGCCAC | GAAGACCCCG | AGGTCCAGTT | CAAGTGGTAC | 780 |
| GTGGACGGCG | TGGAGGTGCA | TAATGCCAAG | ACAAAGCTGC | GGGAGGAGCA | GTACAACAGC | 840 |
| ACGTTCCGTG | TGGTCAGCGT | CCTCACCGTC | CTGCACCAGG | ACTGGCTGAA | CGGCAAGGAG | 900 |
| TACAAGTGCA | AGGTCTCCAA | CAAAGCCCTC | CCAGCCCCCA | TCGAGAAAAC | CATCTCCAAA | 960 |
| GCCAAAGGAC | AGCCCCGAGA | ACCACAGGTG | TACACCCTGC | CCCCATCCCG | GGAGGAGATG | 1020 |
| ACCAAGAACC | AGGTCAGCCT | GACCTGCCTG | GTCAAAGGCT | TCTACCCCAG | CGACATCGCC | 1080 |
| GTGGAGTGGG | AGAGCAATGG | GCAGCCGGAG | AACAACTACA | ACACCACGCC | TCCCATGCTG | 1140 |
| GACTCCGACG | GCTCCTTCTT | CCTCTACAGC | AAGCTCACCG | TGGACAAGAG | CAGGTGGCAG | 1200 |
| CAGGGGAACA | TCTTCTCATG | CTCCGTGATG | CATGAGGCTC | TGCACAACCG | CTACACCCAG | 1260 |
| AAGAGCCTCT | CCCTGAGTAC | TGGTAAACCC | ACCCTGTACA | ACGTGTCCCT | GGTCATGTCC | 1320 |
| GACACAGCTG | GCACCTGCTA | C | | | | 1341 |

(2) INFORMATION FOR SEQ ID NO: 8:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: IGA tailpiece - AA (ix) SEQUENCE DESCRIPTION: SEQ ID NO: 8:

Pro Thr His Val Asn Val Ser Val Val Met Ala Glu Val Asp Gly Thr
                 5                  10                  15
Cys Tyr
   18

(2) INFORMATION FOR SEQ ID NO: 9:

(i) SEQUENCE CHARACTERISTICS:
       (A) LENGTH: 18 amino acids
       (B) TYPE: amino acid
       (C) STRANDEDNESS: single
       (D) TOPOLOGY: linear

```
        (ii) MOLECULE TYPE: IGM tailpiece - AA (ix) SEQUENCE DESCRIPTION: SEQ ID NO: 9:

Pro Thr Leu Tyr Asn Val Ser Leu Val Met Ser Asp Thr Ala Gly Thr
                  5                  10                  15

Cys Tyr
     18

(2) INFORMATION FOR SEQ ID NO: 10:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: Tailpiece - AA (ix) SEQUENCE DESCRIPTION: SEQ ID NO: 10:

Ser Gln Cys Pro Trp Ser Pro Leu Val Leu Gln Asp Ser Asp Thr Tyr
                  5                  10                  15

Leu His Pro Ser Leu Cys Lys
                 20

(2) INFORMATION FOR SEQ ID NO: 11:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: Tailpiece - AA (ix) SEQUENCE DESCRIPTION: SEQ ID NO: 11:

Cys Pro Trp Ser Pro Leu Val Leu Gln Asp Ser Asp Thr Tyr Leu His
                  5                  10                  15

Pro Ser Leu Cys Lys
             20
```

RH HYBRID ANTIBODY

This invention was made with Government support under Grant (or Contract) No. CA 16858, awarded by the NIH. The Government has certain rights in this invention.

BACKGROUND OF THE INVENTION

1. Field of the Invention

The present invention relates, generally to antibodies to Rh(Rhesus) factors which are present on the surface of red blood cells. More particularly, the invention is directed to improved Rh antibodies which may be used in Rh typing methods or as therapeutic agents.

2. Description of Related Art

The publications and other reference materials referred to herein to describe the background of the invention and to provide additional details regarding its practice are hereby incorporated by reference. For convenience, the reference materials are numerically referenced and identified in the appended bibliography.

Rh factors are genetically determined antigens (agglutinogens) which are present on the surface of red blood cells. Rh factors form a complex blood group system which is of major importance in clinical medicine. The Rh(D) antigen is one of the most immunogenic and best known Rh factors. The presence or absence of Rh(D) antigen is especially important in blood transfusions because mixing of Rh(D) positive and Rh(D) negative blood types can result in blood clotting and other severe problems for the blood recipient. Rh(D) blood type is also important in pregnancy where severe problems can occur when the mother and fetus have Rh(D) blood types which do not match.

A number of methods have been developed to determine Rh blood type. The majority of the procedures are hemagglutination tests which utilize one or more reagents that include antibodies to Rh antigens. Typically, the reagents are added to a sample of red blood cells in a test well and incubated for a set period of time. The presence of Rh antigen is most often determined macroscopically by agglutination of the cells in the same manner as other conventional blood typing procedures.

Several modalities and antibody reagents are currently available to perform Rh hemagglutinin tests. In one type of test protocol, IgG anti-Rh antibodies are initially added to the red blood cells. IgG antibodies are "incomplete" antibodies with respect to the Rh antigen and therefor are not able to agglutinate the red blood cells by themselves. As a result, potentiating agents such as non-specific proteins or secondary anti-human IgG must be added to induce a positive agglutination reaction. This type of test is prone to false positives due to the non specific nature of the added potentiating agent.

In another type of Rh typing protocol, IgM anti-Rh antibodies are used in place of the IgG antibody. IgM is a complete antibody with respect to Rh and is capable of agglutinating Rh positive cells. However, IgM antibodies are not nearly as reactive as IgG antibodies. This results in the need for extended incubation times and the potential for false negative tests.

The basic Rh hemagglutination tests have been modified in a number of different ways in order to simplify the tests and make them more accurate. For example, a "gel test" has been proposed which uses a recombinant anti-Rh(D)Fab/phage and anti-M13phage antibody as the secondary reagent. Alternatively, IgG anti-D has been pretreated with reducing agents to open the hinge region of the molecule. Also, red blood cells have been treated with certain enzymatic preparations, such as papain, to render the cells susceptible to direct agglutination with IgG anti-Rh(D). Exemplary Rh(D) blood typing procedures are set forth in Reference Nos. 1–11.

Although the existing procedures for determining Rh blood type are well-suited for their intended purpose, there is still room for improvement. Accordingly, there is a continuing need to develop new reagents and protocols which will make Rh phenotyping even easier, faster and more accurate.

Rh(D) antibodies are also used as prophylactic agents. For example, the administration of Rh(D) antibodies for preventing the hemolytic disease of the newborn due to Rh incompatibility (HDN-Rh) is a very effective, and well established medical practice. HDN-Rh occurs to Rh(D) positive fetuses carried by previously immunized, Rh(D) negative, pregnant women. Rh(D) antibodies of the immunoglobulin G (IgG) class existing in the maternal blood cross the placental barrier and reach the fetal circulation. Once there, Rh(D) antibodies bind to and induce lysis of red blood cells, causing the disease. Since 1961 it is known that the administration of Rh(D) antibodies to pregnant women just after delivery prevents Rh(D) sensitization. More recently and based on accumulated evidence of Rh immunization during pregnancy, antenatal administration of Rh(D) antibodies (at 28 week's gestation) has also been proposed, and adopted in some countries. Despite its efficacy, the mechanism of action of the administered Rh(D) antibodies is not completely understood.

At the time of introduction of the Rh prophylaxis programme, the Rh(D) immunoglobulin for injection was derived mainly from the post-partum plasma of women immunized by pregnancy. Due to the success of this treatment the diminishing number of women immunized during pregnancy has reduced the availability of plasma-derived anti-D. This shortage lead to the recruitment and immunization of D negative male volunteers for the procurement of anti-D. Currently, anti-D used in prophylaxis is composed of immunoglobulin obtained almost entirely from these two sources.

Several considerations suggest that additional, non-plasma derived, sources of anti-D will be required in the near future. Firstly, the demand is expected to increase as the population grows. Secondly, the number of immunized, pregnant women donors is expected to diminish even more due to the efficacy of the Rh prophylaxis. Thirdly, immunization of D negative volunteers has been criticized due to potential risks of contamination with pathogenic, blood-borne viruses. An alternative approach to producing human anti-D is the monoclonal and recombinant antibody technologies.

SUMMARY OF THE INVENTION

In accordance with the present invention, improved Rh antibodies are provided which may be used as therapeutic agents. The improved Rh anti-bodies may also be used in a one-step hemagglutinin method which utilizes a single Rh antisera to provide fast and accurate Rh phenotyping of blood.

The invention is based on the discovery that polymeric functionality can be added to existing IgG anti-Rh antibodies to provide hybrid Rh antibodies which have the desired high level of reactivity with Rh antigens and the ability to agglutinate red blood cells without a separate potentiating agent.

The invention includes reagents adapted for therapeutic use and for use in testing red blood cells for the presence of one or more Rh factors. The reagent includes an anti-Rh hybrid antibody which is composed of IgG antibody with a polymeric tailpiece. In an exemplary embodiment, the hybrid antibody is made up of an IgG3 anti-Rh(D) antibody which includes lambda light chains and gamma-3 heavy chains. The hybrid is formed by attaching an IgM tailpiece to the carboxy terminal end of each of the gamma-3 heavy chains of the IgG3. It was discovered that attachment of the IgM tailpieces to the IgG3 heavy chains produced an antibody which is especially well-suited for Rh phenotyping. The antibody retains high reactivity with Rh(D) antigens while at the same time achieving agglutination of the red blood cells to allow macroscopic evaluation of Rh(D) antigen presence.

As a feature of the present invention, the polymeric tailpiece which is attached to the carboxy terminal end of the IgG antibody may include IgM, IgA or hybrid or synthetic tailpieces. The polymeric tailpiece may also be any amino acid or short peptide which renders the IgG polymeric. Preferred embodiments of the invention are disclosed wherein an IgM tailpiece having 18 amino acids as set forth in SEQ. ID. NO. 5 is utilized. In addition, a preferred IgG3 antibody is disclosed which has gamma-3 heavy chain (SEQ. ID. NO. 6) as well as a preferred lambda light chain (SEQ. ID. NO. 4).

The improved antibodies in accordance with the present invention are used in a one-step hemagglutinin test protocol wherein red blood cells are contacted with a single antisera containing the hybrid IgG anti-Rh antibody. In accordance with conventional one-step typing procedures, the hybrid antisera is contacted with the red blood cells for a sufficient time and at a sufficient temperature to cause agglutination of red blood cells which have one or more Rh factors present. The presence or absence of the Rh factors is determined macroscopically in accordance with established visual protocols for determining agglutination.

The hybrid antibodies of the present invention also have potential to be used as prophylactic agents in HDN-Rh. For the reasons explained above, monoclonal or recombinant anti-Rh(D) will probably be required in the near future to replace polyclonal anti-Rh(D) in the prophylaxis of HDN-Rh. In vivo studies are currently in progress to test the feasibility of this approach, and evidence has been found that monoclonal IgG1 and IgG3 anti-D could indeed replace the commercial polyclonal material. Although the mechanism of action of anti-D antibodies in preventing Rh isoimmunization has not been clearly established, it is generally accepted that rapid clearance or sequestration of anti-D coated, Rh(D)-bearing red blood cells from the maternal circulation is important. It is also assumed that the interaction of the Fc portion of IgG anti-Rh antibodies with Fc receptors (FcR) displayed by certain cell populations is critical for the accelerated red blood cell clearance, this interaction inducing processes like phagocytosis and antibody-dependent cell citotoxicity (ADCC). Polymeric IgGs have been shown to exhibit accelerated clearance and enhanced interactions with FcRs compared to monomeric IgGs.

The above discussed and many other features and attendant advantages of the present invention will become better understood by reference to the following detailed description when taken in conjunction with the accompanying drawings.

DETAILED DESCRIPTION OF THE INVENTION

The present invention involves improving the usefulness of IgG anti-Rh antibodies which are used in hemagglutinin tests to establish the presence or absence of Rh factors. The invention involves the discovery that attaching a polymeric tailpiece to the carboxy terminus of the IgG antibody produces a hybrid antibody which is capable of agglutinating red blood cells.

The IgG antibody which can be modified in accordance with the present invention can be any of the IgG antibodies which are used in Rh typing assays or in Rh-based therapeutic procedures. IgG3 antibodies are preferred. Other IgG antibodies to which polymeric tailpieces can be attached include IgG1, IgG2, and IgG4 generated in conjunction with either kappa or lambda light chains. The IgG3 antibodies may be prepared in accordance with any of the conventional procedures for producing monoclonal or polyclonal antibodies.

Figure 1:
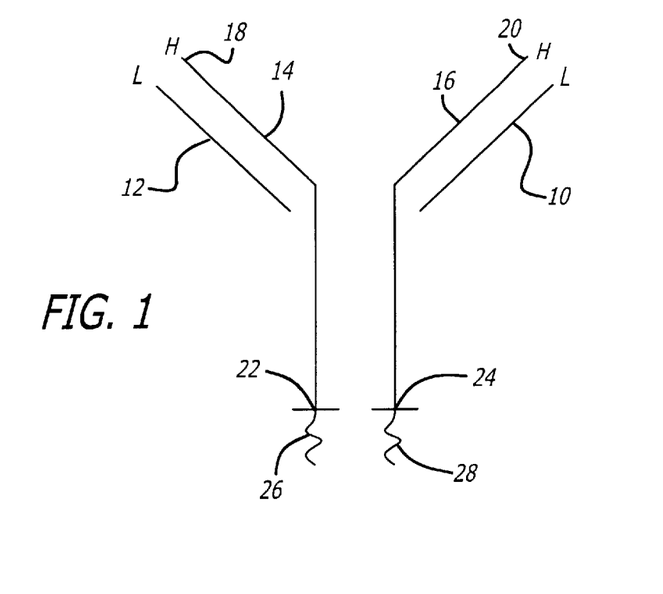
FIG. 1 is a schematic representation of an exemplary IgM/IgG3 anti-Rh(D) hybrid antibody in accordance with the present invention.

A polymeric exemplary IgM/IgG3 hybrid anti-Rh(D) antibody in accordance with the present invention is shown diagrammatically in FIG. 1. The hybrid antibody includes an IgG3 anti-Rh(D) antibody which includes lambda light chains 10 and 12 and gamma-3 heavy chains 14 and 16. The gamma-3 heavy chains 14 and 16 each have an amino terminal end 18 and 20, as well as carboxy terminal ends 22 and 24, respectively. As a feature of the present invention, IgM tailpieces 26 and 28 are attached to the carboxy terminal ends 22 and 24, respectively. A particularly preferred IgG3 antibody is one wherein the light chains 10 and 12 both have the amino acid sequence set forth in SEQ. ID. NO. 4. The heavy chains 14 and 16 for the preferred IgG3 antibody have the amino acid sequence set forth in SEQ. ID. NO. 6.

The IgM tailpieces 26 and 28 both preferably have the same amino acid sequence for a given antibody. In addition to IgM tailpieces, suitable polymeric tailpieces include IgA, hybrids of IgA and IgM and short peptides having from 1 to 30 amino acids. Exemplary tailpieces include:

| | |
|---|---|
| PTHVNVSVVMAEVDGTCY (IgA) | (SEQ. ID. NO. 8) |
| PTLYNVSLVMSDTAGTCY (IgM) | (SEQ. ID. NO. 9) |
| SQCPWSPLVLQDSDTYLHPSLCK (Reference 22) | (SEQ. ID. NO.10) |
| CPWSPLVLQDSDTYLHPSLCK (Reference 22) | (SEQ. ID. NO.1 1) |

Indeed any tailpiece with an accessible cysteine residue would be expected to suffice. Tailpieces 26 and 28 having the amino acid sequence set forth in SEQ. ID. NO. 5 are preferred.

The hybrid antibodies in accordance with the present invention are preferably made utilizing recombinant techniques as set forth in detail in references 12 and 13. The hybrid antibodies are made using these established procedures for genetically engineering the light chain and heavy chain genes to produce antibodies having the desired amino acid sequences.

Figure 2:
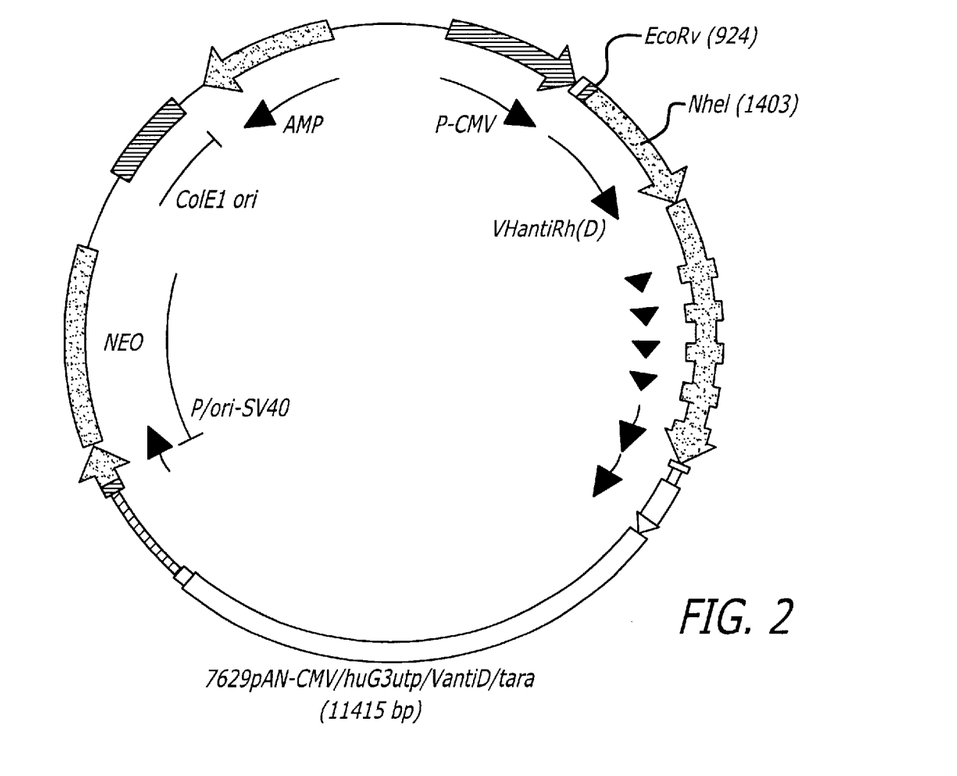
FIG. 2 is a restriction map of the vector used to express the heavy chain of a preferred exemplary antibody (SEQ. ID. NOS. 1 and 2).
Figure 3:
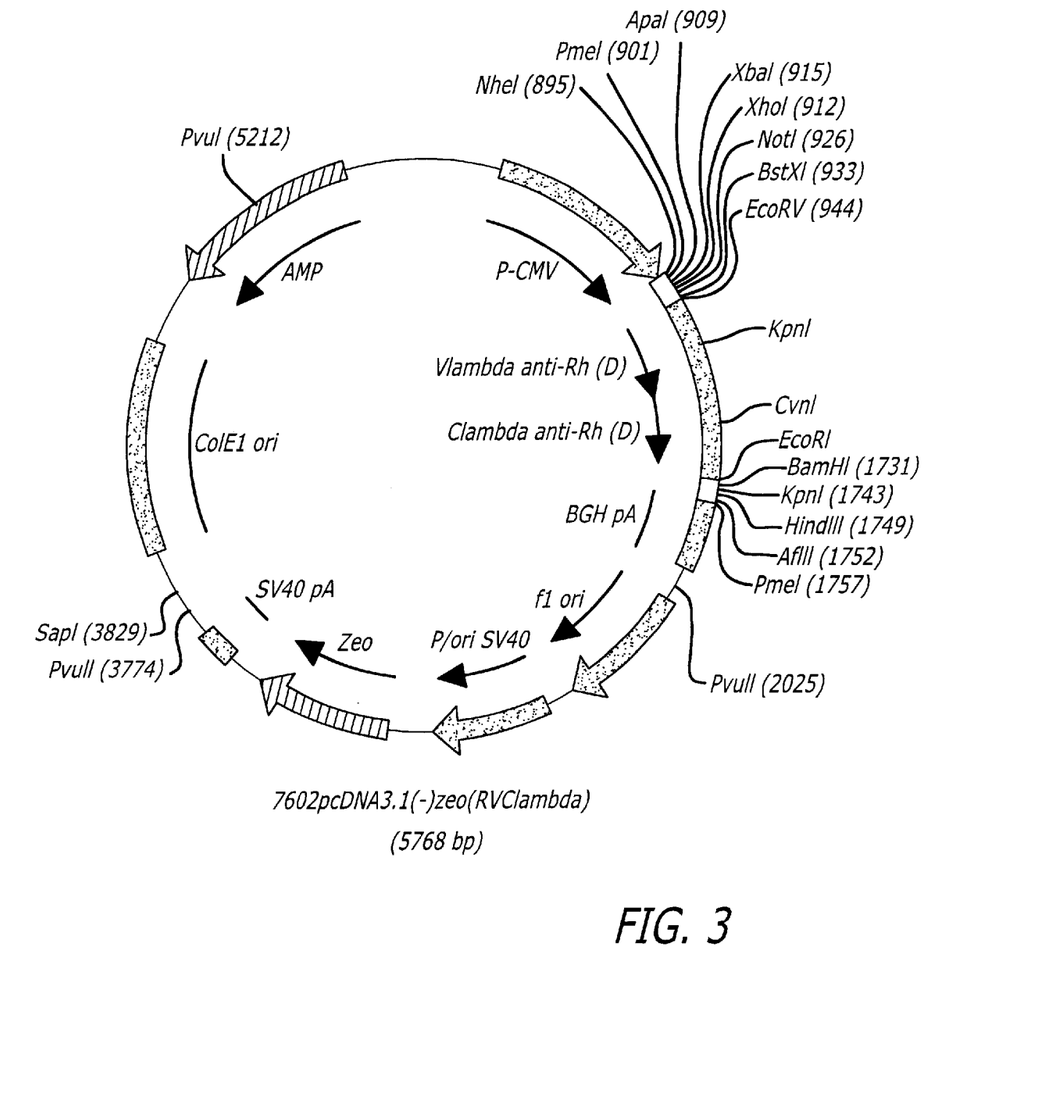
FIG. 3 is a restriction map depicting the vector used to express the light chain of a preferred exemplary hybrid antibody (SEQ. ID. NOS. 3 and 4).

A detailed description of an exemplary procedure for producing a preferred antibody is set forth as follows. This preferred hybrid antibody will be referred to as RecPolRhD. This recombinant antibody has heavy chains with amino acid sequences as set forth in SEQ. ID. NO. 2 and light chains with amino acid sequences as set forth in SEQ. ID. NO. 4. This recombinant antibody was synthesized and secreted into tissue culture media by a transfectoma generated by sequential transfection of the antibody light chain (pAZ7602) and heavy chain (pAN7629) containing vectors (see FIGS. 3 and 2, respectively) into the Chinese Hamster Ovary (CHO) cell line Pro-5 (ATCC CRL 1781). The details of this exemplary procedure are as follows:

1) Construction of light chain expression vector: The variable and constant domain encoding genes of a human monoclonal anti-Rh(D) antibody (named D19) light chain were separately amplified from cDNA by the polymerase chain reaction (RT-PCR). After identification by restriction enzyme digestion and DNA sequencing analysis both gene fragments were rejoined by overlapping PCR, using primers containing restriction sites to facilitate cloning into the selected eukaryotic expression vector pcDNA3.1. The amplification product of the second PCR reaction was cloned into pCRBlunt. Positive identification was repeated in a similar fashion, and the identified entire light chain gene was subcloned into the expression vector.

2) Construction of heavy chain expression vector: The variable domain of a human monoclonal anti-Rh(D) antibody (D19) heavy chain was amplified by standard RT-PCR. Restriction enzyme digestion and DNA sequencing analysis was done to positively identify the VH gene. A new PCR was performed using primers containing a splice recognition sequence in the 3'-end primer, and restriction sites to facilitate cloning into the selected eukaryotic expression vector. The expression vector was built by combining selected sequences of two previously described vectors, pAH4802 and pAG4006. pAH4802 is an expression vector containing cloning sites (EcoRV/NheI) for heavy chain variable regions, and all of the information corresponding to the constant part of the gamma 3 heavy chain. pAG4006 contains information encoding a recombinant gamma 3 heavy chain specific for the hapten molecule dansyl. This recombinant gamma 3 heavy chain has a mu-tail piece attached to its carboxy terminus. A three-way ligation reaction was performed using the HindIII/SacII fragment of pAH4802 (containing the $V_\pi$ cloning sites and most of the _3 heavy chain sequence), the SacII/BamHI fragment of pAG4006 (containing the 3'-end of the gamma 3 heavy chain with the mu-tail piece), and pUC 18 (digested with HindIII and BamHI) as a backbone. The resulting intermediate vector, pUC18-7605int, was digested with BamHI and HincII. To build a generic expression vector, the BamHI/HincII fragment (containing the gamma 3 heavy chain with the mu-tail piece, and with cloning sites EcoRV/NheI for any desired $V_\pi$) was inserted into pAN7608, which is a modified version of pcDNA3.1 where the neomycin resistance gene is the selectable marker and the short segment NheI-XbaI has been excised from the polylinker. The cloned VH sequence specific for the Rh(D) antigen was subcloned into this vector as a EcoRV/NheI fragment to generate pAN7629, which is the final expression vector.

The above procedure for preparing an IgM/IgG hybrid antibody is exemplary only, with it being understood that other anti-Rh antibodies may be modified in the same manner by adding a polymeric tailpiece.

The hybrid antibody may be used in the same manner as any antiserum that is used in a single-step blood typing method. The antibody may be suspended in a variety of standard carrier solutions including saline or PBS. The concentration of hybrid antibody in the solution may be varied to achieve desired antigen reactivity and agglutination properties. The amount of antibody in a given solution can be varied based on simple experimental evaluation of the agglutination titer.

An advantage of the present invention is that the hybrid antibody can be simply mixed with the red blood cells being typed and allowed to incubate at room temperature for a short period of time. The incubation period is generally on the order of a few minutes up to an hour. The sample is then visually checked for agglutination to establish the blood is Rh-positive or negative. Two exemplary Rh-typing methods in accordance with the present invention are as follows:

1. Spin technique (in tubes):
   In a glass tube add 2 drops of Rh(D) antibody and 1 drop of a 3% red blood cell suspension made in saline solution. Rh(D) antibody can be used either as previously titrated culture supernatant or as properly quantified purified protein. Saline solution is 0.15 M NaCl.
   Incubate for 30 minutes at room temperature or 10–15 minutes at 37° C.
   Centrifuge at 1000 g for 40 seconds.
   Examine macroscopically, over a light source, for agglutination by gently tapping or shaking and rolling the tube to remove the cell button from the bottom.
   Record the score for agglutination.

2. Rh(D) typing using u-well microplates:
   Add 25 microL of each of the different red blood cell samples to test (3% suspensions made up in saline or phosphate buffered saline solution) to a well containing 50 microL of Rh(D) antibody (as previously titrated culture supernatant or quantified purified protein). Mix well by gentle shaking.
   Cover the plate with a lid and incubate at 37° C. for 15 minutes.
   Lightly centrifuge the plate at 100 g for 30–60 seconds.
   Agglutination can be read by tilting the plate at an angle of 70 degrees to the horizontal and allowing the cells to "trail"; with positive reactions the cell button remains in the bottom of the well, negative reactions run or trail. Reactions can also be read by looking for agglutination after resuspending the cell button. Resuspension can be achieved by tapping the plates.

The hybrid antibodies of the present invention may also be used as prophylactic agents. As already mentioned, the administration of Rh(D) antibodies for preventing the hemolytic disease of the newborn due to Rh incompatibility (HDN-Rh) is an effective and established medical practice. However, traditional sources of the anti-D immunoglobulin for injection from the post-partum plasma of women immunized by pregnancy and from immunized D negative male are becoming limited. Currently, anti-D used in prophylaxis is composed of immunoglobulin obtained almost entirely from these two sources.

Considering that additional, non-plasma derived, sources of anti-D will certainly be required in the near future, the monoclonal and recombinant antibody technologies may provide an alternative approach to producing the required antibodies. Monoclonal anti-Rh(D) will probably be necessary to replace polyclonal anti-Rh(D) in the prophylaxis of HDN-Rh. It is generally accepted that rapid clearance or sequestration of anti-D coated, Rh(D)-bearing red blood cells from the maternal circulation is important to prevent Rh(D) sensitization of mothers at risk. The rapid clearance of polymeric IgGs make polymeric IgG anti-Rh(D) potentially potent for use as a prophylactic reagent in HDN-Rh, either alone or in conjunction with other monoclonal antibody(ies).

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

BIBLIOGRAPHY

1) U.S. Pat. No. 5,723,293
2) U.S. Pat. No. 5,653,978
3) U.S. Pat. No. 4,403,042
4) U.S. Pat. No. 4,319,882
5) U.S. Pat. No. 4,358,436
6) U.S. Pat. No. 4,851,210
7) P. L. Mollison, C. L. Engelfriet, and M. Contreras, Blood transfusion in clinical medicine, *Blackwell Scientific Publications*, Oxford, 1993.
8) I. Chanarin Ed. Laboratory haematology, an account of laboratory techniques, 1989.
9) Dziegel M. et al., Phage display used for gene cloning of human recombinant antibody against the erythrocyte surface antigen, rhesus D., *J. Immunol. Methods* 182:7, 1995.
10) Siegel, D. L. et al., Isolation of cell surface-specific human monoclonal antibodies using phage display and magnetically-activated cell soring: application in immunohematology. *J. Immunol. Methods*, 206:73, 1997.
11) Lapierre, J. et al., Transfusion, 30:109, 1990.
12) Smith, R. I. F. et al., Recombinant Polymeric IgG: An Approach to Engineering More Potent Antibodies, *Bio/Technology*, 12:683–688, 1994.
13) Siegel D. L. The human immune response to red blood cell antigens as revealed by repertoire cloning. *Immunol. Res.* 17:239, 1998.
14) Voak D. Monoclonal antibodies as blood grouping reagents. Bailliere's *Clinical Haematology* 3:219–42; 1990.
15) Hughes-Jones N. C. Human monoclonal antibodies and haemolytic disease of the newborn. *Brit. J. Haematol.* 70:263–5, 1988.
16) Thompson K. M and N. C. Hughes-Jones. Production and characterization of monoclonal anti-Rh. *Bailliere's Clin. Haematol.* 3:243–53, 1990.
17) Hughes-Jones N. C. and S. F. Parsons. Monoclonal antibodies to red cell alloantigens with particular reference to Anti-D. *Trans. Med. Rev.* VI:191–200, 1992.
18) McCann M. C., K. James and B. M. Kumpel. Production and use of human monoclonal anti-D antibodies. *J. Immunol. Meth*. 115:3–15 (1988).
19) Bowman J. M. The prevention of Rh immunization. *Trans. Med. Rev.* 2:129–50, 1988.
20) Smith, R. I. F. et al., Addition of a Tailpiece to IgG Results in Polymeric Antibodies with Enhanced Effector Functions Including Complement-Mediated Cytolysis by IgG4, *J. Immunol.* 154:2226–2236, 1995.
21) Coloma M. J. et al., Novel vectors for the expression of antibody molecules using variable regions generated by PCR. *J. Immunol. Meth*. 152:89–104, 1992.
22) French, D. L et al. The Molecular and biochemical characterization of mutant monoclonal antibodies with increased antigen binding. *J. Immunol* 14:2918–22, 1991.
23) Kumpel B. M. and D. J. Jackson, Characterization and functional activity of human Rh monoclonal antibodies. *Trans. Clin. et Biol.* 6:453–8, 1996.
24) Chapman G. E., A phamacokinetic/pharmacodinamic model for the action of anti-D immunoglobulin in effecting circulatory clearance of Rh D+ red cells. *Trans. Med.* 6:227–33, 1996.
25) Kumpel B. M., Coordinator's report: an assessment of the functional activity of human Rh monoclonal antibodies after their evaluation by nine laboratories. *Trans. Clin. et Biol.* 6:439–52, 1996.

What is claimed is:

1. A reagent for use in a hemagluttin test to determine the presence of one or more Rh antigens on red blood cells, said reagent comprising:

an IgG anti-Rh antibody which comprises two light chains and two heavy chains wherein said heavy chains each comprise an amino terminal end and a carboxy terminal end, and wherein said light chains comprise lambda light chains and said heavy chains comprise gamma 3 heavy chains, said gamma 3 heavy chains each consisting of a polypeptide having the amino acid sequence set forth in SEQ. ID. NO. 6 and said lambda light chains each consisting of a polypeptide having the amino acid sequence set forth in SEQ. ID. NO. 4; and a polymeric tailpiece attached to the carboxy terminal end of each of said heavy chains, said polymeric tailpiece consisting of a polypeptide having the amino acid sequence set forth in SEQ. ID. NO. 5.

2. A method for testing red blood cells to determine the presence of one or more Rh factors, said method comprising the steps of:

(a) contacting red blood cells with an engineered antibody which comprises an IgG anti-Rh hybrid antibody, said contact being for a sufficient time and at a sufficient temperature to cause agglutination of red blood which have one or more Rh factors present, and where said hybrid antibody comprises:

an Ig anti-Rh antibody which comprises two light and two heavy chains, wherein said heavy chains each comprise an amino terminal end and a carboxy-terminal end and wherein said light chains comprise lambda light chains and said heavy chains comprise gamma 3 heavy chains, said gamma 3 heavy chains each consisting of a polypeptide having the amino acid sequence set forth in SEQ. ID. NO. 6 and said lambda light chains each consisting of a polypeptide having the amino acid sequence set forth in SEQ. ID. NO. 4; and a polymeric tailpiece attached to the carboxy terminal end of each of said heavy chains said polymeric tailpiece consisting of a polypeptide having the amino acid sequence set forth in SEQ. ID. NO. 5; and (b) determining whether said red blood cells agglutinate as a result of said contact with said IgG anti-Rh hybrid antibody to determine the presence of one or more Rh factors.

* * * * *